United States Patent [19]
Gordon et al.

[11] Patent Number: 6,057,360
[45] Date of Patent: May 2, 2000

[54] COMPOSITIONS AND SYSTEMS FOR THE TREATMENT OF HYPERPIGMENTATION

[76] Inventors: Benjamin D. Gordon, 14 Hillsea Rd., Yarmouth Port, Mass. 02675; Eugene Gans, 4343 E. Camelback Rd., #250, Phoenix, Ariz. 85018

[21] Appl. No.: 09/286,405

[22] Filed: Apr. 5, 1999

Related U.S. Application Data

[63] Continuation of application No. 08/906,351, Aug. 5, 1997, Pat. No. 5,932,612.

[51] Int. Cl.⁷ .......................... A01N 43/16; A61K 31/355
[52] U.S. Cl. .......................... 514/458; 514/474; 514/846; 424/401; 424/62
[58] Field of Search ..................... 514/458, 474, 514/846; 424/401, 62

[56] References Cited

U.S. PATENT DOCUMENTS 5,262,153  11/1993  Mishima et al. ......................... 424/62
5,932,612   8/1999  Gordon et al. .......................... 514/458

OTHER PUBLICATIONS

Chemical Abstracts 121:91353, "Cosmetics for Rough Skin", May 1994.

Chemical Abstracts 111:160007, "Skin–Lightening Cosmetics Vitamin E Acetate and Unsaturated Fatty Acids", Apr. 1989.

110:218836, "Skin–Lightening Cosmetics Containing L–Ascorbic Acid Derivatives", Feb. 1989.

*Primary Examiner*—Frederick Krass
*Attorney, Agent, or Firm*—William J. McNichol, Jr.

[57] ABSTRACT

A novel skin lightening preparation and its method of use are described. The composition and method are characterized by reduced skin irritation, while providing skin lightening that is at least as effective as known over-the-counter preparations.

25 Claims, No Drawings

COMPOSITIONS AND SYSTEMS FOR THE TREATMENT OF HYPERPIGMENTATION

This Application is a continuation of application Ser. No. 08/906,351 filed Aug. 5, 1997, now U.S. Pat. No. 5,932,612.

FIELD OF THE INVENTION

This invention relates to pigmentation disorders, specifically hyperpigmentation.

BACKGROUND OF THE INVENTION

Melanin, a pigment found in human skin, is produced by cells known as melanocytes. Melanocytes produce melanin in granules called melanosomes. Melanosomes are transferred from the metanocytes to keratinocytes, a layer of keratin-producing cells that is closer to the outer surface of the skin. The more melanosomes that are transferred to the keratinocytes, the darker the skin appears. This process can be altered in persons of any skin type or race. Alteration that results in excessive darkening is known as hyperpigmentation.

Hyperpigmentation can take a variety of forms. Melasma is a form of hyperpigmentation in pregnant women that is characterized by dark patches on the cheeks and forehead, and is sometimes called "pregnancy mask". With age, many persons develop dark spots sometimes known as "liver spots." Hyperpigmentation is sometimes a side effect of birth control pills, and can be a persistent result of acne, burns, bites and other skin injuries.

The only treatment for hyperpigmentation that is approved in the United States for use by consumers without a prescription is the topical application of 1,4benzenediol, also known as hydroquinone. It acts by suppressing melanocyte activity. Hydroquinone, by itself or in combination with glycolic acid, is sold without prescription at strengths of up to 2% and at strengths of up to 4% by prescription. Hydroquinone preparations are effective, but not without drawbacks. They can cause burning, redness, sensitization and irritation in some persons. Close supervision of the patient by a physician is recommended when prescription strength preparations are used. It is desirable to provide a treatment for hyperpigmentation that is at least as effective as hydroquinone, but lacks hydroquinone's side effects.

SUMMARY OF THE INVENTION

We have discovered that a combination of (1) tocopherol, or its dermally available derivatives, (2) a derivative of ascorbic acid, and (3) a fatty acid, can be used to treat hyperpigrnentation. This combination is at least as effective as over the counter hydroquinone preparations, with dramatically reduced side effects. It is effective in treating hyperpigmentation once it occurs, as well as in the prevention of hyperpigmentation.

DETAILED DESCRIPTION OF THE INVENTION

Tocopherol, also known as Vitamin E, is well known and commercially available. Dermally available derivatives of tocopherol may also be used in this invention. A dermally available derivative of tocopherol is a compound that makes tocopherol or a biological active form of tocopherol available to the skin. In preparing compositions in accordance with the invention, tocopherol acetate was used as the source of tocopherol, although free tocopherol, tocopherol linoleate or other sources can be used.

A variety of derivatives of ascorbic acid can be used in this invention, among them ascorbityl palmitate, magnesium ascorbityl phosphate, and ascorbityl linoleate. However, lipid esters, especially ascorbityl palmitate, are preferred.

Either $C_{18}$ unsaturated fatty acids, such as oleic, linoleic and linolenic acids, or other essential fatty acids, including arachadonic acid, may be used in connection with this invention. However, linoleic acid is preferred. In the embodiments described below, linoleic acid was used.

These three components, together with appropriate carriers or vehicles, can be compounded into dermatologically useful liquid, gel or cream products as follows:

TABLE I

| Ingredients | Percentage w/w | | |
|---|---|---|---|
| | Liquid | Gel | Cream |
| (1) Ascorbyl Palmitate | 1.50 | 1.50 | 1.50 |
| (2) Tocopherol Acetate | 2.00 | 1.00 | 1.00 |
| (3) Linoleic Acid | 4.00 | 4.00 | 2.00 |
| (4) Safflower Oil | 20.00 | 17.75 | 3.00 |
| (5) Oleyl Alcohol | 12.00 | 12.00 | 4.00 |
| (6) Jojoba Oil | 20.00 | — | 1.00 |
| (7) SDA 40 Anhydrous Alcohol | 12.00 | 12.00 | 8.00 |
| (8) Benzyl Alcohol | .0.50 | 0.50 | 0.50 |
| (9) BHA | 0.50 | 0.50 | 0.50 |
| (10) Cyclomethicone | 27.95 | 16.60 | — |
| (11) Sodium Bisulfite | — | 0.15 | 0.15 |
| (12) Sorbitan Laurate | — | 2.00 | — |
| (13) C18–C36 Acid Glycol Ester | — | 5.00 | — |
| (14) Tribehenin | — | 5.00 | — |
| (15) Petrolatum | — | 7.50 | 3.00 |
| (16) Behenyl Erucate | — | 15.00 | — |
| (17) PEG-4 Diheptanoate | — | — | 5.00 |
| (18) Glyceryl Stearate SE | — | — | 4.00 |
| (19) Cetyl Alcohol | — | — | 1.80 |
| (20) Polyacrylamide (and) C13–14 Isoparaffin (and) Laureth-7 | — | — | 2.00 |
| (21) Hydroxyethylcellulose | — | — | 0.20 |
| (22) Water | — | — | to 100% (62.80) |

The liquid is prepared as follows. Part A is prepared by warming to 40° C. and dissolving components (1) and (9) in, components (5), (7) and (8). This is covered while Part B is prepared by separately mixing components (2), (3), (4) and (6) which are warmed to 40° C. Parts A and B are then mixed and cooled to ambient temperature. Component (10) is added and mixed until uniform.

The gel is prepared as follows. Part A is prepared by warming to 45° C. and dissolving components (1) and (9) in components (5), (7) and (8), and then adding component (11). This is then stirred and covered. Part B is prepared by heating to 70° C. and mixing until fluid and uniform, components (12), (13), (14), (15) and (16), which are then cooled to 55° C. and components (2), (3), and (4) are then added. Part A is added to Part B, with minimize air incorporation, and cooled to 40° C. and filled into containers.

The cream is prepared as follows. Part A is prepared by separately heating to 70° C. and mixing until fluid and uniform components (3), (4), (6), (15), (16) and (19). Component (2) is added to Part A just before adding Part B. Part B is prepared by heating component (20) to 70° C., and adding and dissolving component (21). Then components (20) and (18) are added and dispersed. Part C is prepared by stirring and then, with either an internal or external homogenizer operating, adding Part B to Part A until uniform. The speed of the homogenizer is then reduced and the temperature lowered to 45° C. Components (1) and (9) are warmed to 45° C. and dissolved in components (5), (7) and (8) which are also warmed to 45° C. Component (11) is then added. This is then stirred to disperse, cooled and added to Part C while stirring.

Optional additional ingredients for all of these formulations include hydroxy acids, hydroquinone (1.5 to 4.0%), fragrances, and other skin lightening, turnover-enhancing, or conditioning agents.

The amount of the composition of this invention that is to be applied to the skin will vary with a number of factors, including the severity of the hyperpigrnentation and the sensitivity of the affected skin area. Consequently, this will be a matter for the clinical judgment of the patient's health care professional. Generally, from about 0.25 g to about 0.50 g of the above described cream should be applied to each 100 cm² of affected skin.

EXAMPLE 1

Melanoderm Assays

The effectiveness of the present invention in the treatment and prevention of hyperpigmentation was demonstrated by use of the Melanoderm assay. The Melanoderm assay is a recognized in vitro assay, performed on skin grown from human epidermal cells in vitro (a "human skin equivalent"). It stimulates melanogenesis by the addition of dopamine, the natural precursor of melanin within skin, producing visual color in the human skin equivalent. The purpose of the Melanoderm assay is two-fold. First, it determines the ability of test materials to inhibit melanogenesis, the formation of melanin. Second, it determines the ability of test materials to reduce pigmentation ("lighten/whiten skin") after melanogenesis has occurred.

In a Melanoderm assay the substance to be tested is combined with the dopamine and resultant changes in the formation of melanin are compared with a positive dopamine control without the test material. Any visible reduction in melanin formation is due to the ability of the test material to inhibit melanogenesis. To determine if a test material also reduces existing pigmentation, the test material is added to the skin equivalent after it has been treated with dopamine to induce pigmentation An active, effective test agent produces a visual reduction in pigmentation.

In the Melanoderm assay, changes in pigment formation and pigment "whitening" are visually confirmed by an experienced investigator. In the assays conducted on the compositions of this invention, it was observed that compositions of the invention blocked visual formation of color after it had been mixed with dopamine, thus indicating that they prevent melanin formation. In addition, the compositions of the invention "whitened" the pigmented human skin equivalent when it was added after pigmentation had been pre-formed, thus indicating that it reduces pre-existing pigmentation.

EXAMPLE 2

Clinical Hyperpigrnentation Studies and Results

The results of the Melanoderm assays is confirmed by the following human, in vivo hyperpigmentation studies where several dose forms of the invention are shown to effectively reduce hyperpigmentation in both Caucasian and black skin. The ability of the invention to reduce visible hyperpigmentation in skin was clinically evaluated using a 0 to 3 clinical rating scale (none to dark) in subjects with either caucasian ("Cau") or black skin ("Bla") having various forms of hyperpigmentation, such as: age spots, sun spots, post-inflammatory & related hyperpigmentation. Each hyperpigmentation spot in a standard sample area was rated on this scale and the sum of these ratings were recorded for each sample area. Subjects applied their test materials twice a day (AM & PM) for period ranging from 12 weeks to 24 weeks. Each of the following studies used a preparation according to this invention that contained tocopherol acetate, ascorbyl palmitate and linoleic acid, incorporated either into a fluid, a gel, or cream base as shown in Table 1. A commercially available 2% hydroquinone cream was used. Each test agent, or a no treatment control, was assigned to a matching site. Hyperpigmentation scoring was done by a blinded investigator at baseline and at each evaluation period.

Clinical Evaluation of a Fluid Formulation of the Invention and a 2% Hydroquinone Cream in Reducing Hyperpigmentation

| Treatment | Number of Subjects | Type Skin | Percent Reduction | | | |
|---|---|---|---|---|---|---|
| | | | 1 mo | 2 mo | 3 mo | 4 mo |
| Invention | 5 | Cau | −31% | −38% | −42% | −49% |
| 2% Hydroquinone | 10 | Cau | −23% | −40% | −40% | −40% |
| Placebo | 10 | Cau | +8% | −23% | −14% | −16% |

Clinical Evaluation of a Cream According to the Present Invention and a 2% Hydroquinone Cream in Reducing Hyperpigmentation

| Treatment | Number of Subjects | Type Skin | Percent Reduction | | | |
|---|---|---|---|---|---|---|
| | | | 1 mo | 2 mo | 3 mo | 4 mo |
| Invention | 8 | Cau | −5% | −15% | −23% | −36% |
| 2% Hydroquinone | 8 | Cau | −17% | −30% | −32% | −35% |
| Placebo | 10 | Cau | +8% | −23% | −14% | −16% |

Clinical Evaluation of a Gel According to the Present invention and a 2% Hydroquinone Cream in Reducing Hyperpigmentation

| Treatment | Number of Subjects | Type Skin | Percent Reduction | | | |
|---|---|---|---|---|---|---|
| | | | 3 wk | 6 wk | 9 wk | 12 wk |
| Invention | 8 | Bla | −34% | −60% | −64% | −63% |
| 2% Hydroquinone | 8 | Bla | −31% | −39% | −47% | −56% |
| Placebo | 4 | Bla | 0 | −16% | −7% | −3% |

Clinical Evaluation of the Invention as a Gel Preparation

This was a 16 week study, in which one or more sites of hyperpigrnentation on each of thirteen subjects with dark skin were treated by application of the gel. The intensity of hyperpigmentation was independently assessed by the investigator and subjects at baseline (zero time) after 16 weeks using the following one to four evaluation scale; even skin tone (trace or no hyperpigmentation); slightly dark; moderately dark; very dark. The results were as follows:

| Degree of Hyperpigmentation | The Number of Subjects At Each Intensity Level | | | |
|---|---|---|---|---|
| | Subject's Ratings | | Investigator's Ratings | |
| | 0 Week | 16 wks | 0 Week | 16 wks |
| Very Dark | 16 | 0 | 3 | 0 |
| Moderately Dark | 18 | 2 | 18 | 0 |
| Slightly Dark | 15 | 23 | 24 | 23 |
| Even Tone | 0 | 25 | 3 | 26 |

Both the investigator and the more self-critical subjects judged the formulation to be very effective.

A study was performed to determine whether the formulations of this invention caused skin irritation. In a three day study, the effect of a commercially available 2% hydroquinone preparation, sodium lauryl sulfate (SLS), and the present invention were compared, along with no treatment. SLS is a known irritatant and was used as a positive control. Both occlusive and non-occlusive applications were made to test areas on the backs of each subject. Skin reaction was evaluated on the Berger & Bowman Clinical Irritation Scale as follows:

Irritation Grading Scale:

0  No evidence of irritation
 1  Minimal erythema, barely perceptible
 2  Definite erythema, readily visible; or minimal edema; or minimal papular response
 3  Erythema, and papules
 4  Definite edema
 5  Erythema, edema, and papules
 6  Vesicular eruption
 7  Strong reaction spreading beyond test site Skin Glazing Scale:

A  Slight glazed appearance
 B  Marked glazing
 C  Glazing with peeling and cracking
 D  Glazing with fissures
 E  Film of dried serous exudate covering all or portion of the patch site
 F  Small petechial erosions and/or scabs Results of the tests were as follows:

| | SUBJECT | | | |
|---|---|---|---|---|
| | No. 1 | No. 2 | No. 3 | No. 4 |
| Occlusive Application: | | | | |
| 2% hydroquinone | 2B | 0 | 2B | 3A |
| Invention | 0 | 0 | 0 | 0 |
| SLS | 3 | 2B | 2B | 0 |
| No Treatment | 0 | 0 | 1A | 0 |
| Non-Occlusive Application: | | | | |
| 2% hydroquinone | 1 | 1 | 0 | 2A |
| Invention | 0 | 0 | 0 | 0 |
| SLS | 0 | 0 | 0 | 0 |
| No Treatment | 0 | 0 | 0 | 0 |

The results show that, for both occlusive and non-occlusive applications, the invention produced no irritation while 2% hydroquinone often caused significant irritation.

We claim:

1. A topical composition comprising effective amounts of:
   a) tocopherol or a dermally available derivative thereof;
   b) a dermally available derivative of ascorbic acid;
   c) a $C_{12}$–$C_{20}$ fatty acid; and
   d) a pharmaceutically acceptable carrier;
   wherein said composition:
   e) reduces hyperpigmentation upon topical application to the skin;
   f) is non-irritating upon topical application to the skin; and
   g) does not contain hydroquinone.

2. The composition of claim 1, wherein the derivative of ascorbic acid is ascorbityl palmitate, ascorbityl linoleate, ascorbityl octanoate, or magnesium ascorbityl phosphate.

3. The composition of claim 1, wherein the fatty acid is an essential fatty acid or an unsaturated fatty acid.

4. The composition of claim 1, wherein the fatty acid is an essential fatty acid or a $C_{16-20}$ unsaturated fatty acid.

5. The composition of claim 2, wherein the fatty acid is an essential fatty acid or a $C_{16}$–$C_{20}$ unsaturated fatty acid.

6. The composition of claim 2, wherein the fatty acid is a $C_{18}$ unsaturated fatty acid.

7. The composition of claim 2, wherein the fatty acid is ioleic acid or oleic acid.

8. The composition of claim 1, wherein the dermally available derivative of tocopherol is tocopherol acetate or tocopherol linoleate.

9. The composition of claim 2, wherein the dermally available derivative of tocopherol is tocopherol acetate or tocopherol linoleate.

10. The composition of claim 4 wherein the dermally available derivative of tocopherol is tocopherol acetate or tocopherol linoleate.

11. The composition of claim 5 wherein the dermally available derivative of tocopherol is tocopherol acetate or tocopherol linoleate.

12. The composition of claim 1 wherein the derivative of ascorbic acid is ascorbityl palmitate, ascorbityl linoleate or magnesium ascorbityl palmitate.

13. The composition of claim 1, wherein the derivative of ascorbic acid is a lipid ester of ascorbic acid.

14. The composition of claim 2, wherein the derivative of ascorbic acid is ascorbityl palmitate, ascorbityl linoleate or magnesium ascorbityl palmitate.

15. The composition of claim 2, wherein the derivative of ascorbic acid is a lipid ester of ascorbic acid.

16. The composition of claim 4, wherein the derivative of ascorbic acid is ascorbityl palmitate, ascorbityl linoleate or magnesium ascorbityl palmitate.

17. The composition of claim 4, wherein the derivative of ascorbic acid is a lipid ester of ascorbic acid.

18. The composition of claim 4, wherein the derivative of ascorbic acid is ascorbityl palmitate, ascorbityl linoleate or magnesium ascorbityl palmitate.

19. The composition of claim 9, wherein the derivative of ascorbic acid is a lipid ester of ascorbic acid.

20. The composition of claim 11, wherein the derivative of ascorbic acid is ascorbityl palmitate, ascorbityl linoleate or magnesium ascorbityl palmitate.

21. The composition of claim 11, wherein the derivative of ascorbic acid is a lipid ester of ascorbic acid.

22. The composition of any one of claims 1 through 21, wherein the tocopherol or its dermally available derivatives are present in about 0.05 to about 10% by weight, the derivative of ascorbic acid is present in about 0.05 to about 10% by weight, and the fatty acid is present in about 0.05 to about 25% by weight.

23. The composition of claim 22, wherein the tocopherol or its dermally available derivatives are present in about 1.0 to about 4.0% by weight, the derivative of ascorbic acid is present in about 1.0 to about 4.0% by weight, and the fatty acid is present in about 1.0 to about 5.0% by weight.

24. The composition of claim 22, wherein the tocopherol or its dermally available derivatives are present in about 1.0 to about 2.0% by weight, the derivative of ascorbic acid is present in about 1.0 to about 2.0% by weight, and the fatty acid is present in about 2.0 to about 4.0% by weight.

25. A method of treating hyperpigmentation comprising administering an effefective amount of the composition of any one of claims 1 through 21 to the skin of a person in need of such treatment.

* * * * *